(12) United States Patent
Mansour et al.

(10) Patent No.: US 8,566,123 B2
(45) Date of Patent: *Oct. 22, 2013

(54) ELECTRONIC PATIENT RECORD DOCUMENTATION WITH PUSH AND PULL OF DATA TO AND FROM DATABASE

(75) Inventors: Richard P. Mansour, Shreveport, LA (US); Lori Mullehhour, Rancho Palos Verdes, CA (US); Ellen Loch, Berwyn, PA (US); Sash Barige, Downington, PA (US); Tyler Downs, West Chester, PA (US); David H. Mitchel, Limerick, PA (US); Jason C. Ipock, Aldan, PA (US); Shiva Kasargod, Edison, NJ (US)

(73) Assignee: Allscripts Software, LLC, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/621,119

(22) Filed: Sep. 15, 2012

(65) Prior Publication Data

US 2013/0080190 A1 Mar. 28, 2013

Related U.S. Application Data

(63) Continuation of application No. 11/142,060, filed on May 31, 2005, now Pat. No. 8,321,241.

(51) Int. Cl.
*G06Q 10/00* (2012.01)
*G06Q 50/00* (2012.01)

(52) U.S. Cl.
USPC .................................................. 705/3; 705/2

(58) Field of Classification Search
USPC ......................................................... 705/2–3
See application file for complete search history.

(56) References Cited

U.S. PATENT DOCUMENTS

| | | | | | |
|---|---|---|---|---|---|
| 5,072,383 | A | * | 12/1991 | Brimm et al. | 705/2 |
| 5,077,666 | A | * | 12/1991 | Brimm et al. | 705/2 |
| 5,208,907 | A | * | 5/1993 | Shelton et al. | 715/200 |
| 5,247,611 | A | * | 9/1993 | Norden-Paul et al. | 715/217 |
| 5,253,361 | A | * | 10/1993 | Thurman et al. | 1/1 |
| 5,253,362 | A | * | 10/1993 | Nolan et al. | 1/1 |
| 5,301,319 | A | * | 4/1994 | Thurman et al. | 1/1 |
| 5,325,478 | A | * | 6/1994 | Shelton et al. | 715/236 |
| 5,781,891 | A | * | 7/1998 | Dvorak et al. | 705/2 |
| 5,924,074 | A | * | 7/1999 | Evans | 705/3 |
| 6,221,012 | B1 | * | 4/2001 | Maschke et al. | 600/301 |
| 6,317,719 | B1 | * | 11/2001 | Schrier et al. | 705/2 |
| 6,338,042 | B1 | * | 1/2002 | Paizis | 705/7.37 |
| 6,421,649 | B1 | * | 7/2002 | Rattner | 705/2 |

(Continued)

*Primary Examiner* — Minnah Seoh
(74) *Attorney, Agent, or Firm* — Tillman Wright, PLLC; Chad D. Tillman; Jeremy C. Doerre

(57) ABSTRACT

A medical records software apparatus and method is described that allows a clinician, e.g., nurse or doctor, to combine entry of new patient orders, prescriptions, flowsheet observations, etc. into the documentation process or workflow. A documentation user interface is provided that pulls patient data from a database into the display. The user can select on the user interface a category of a patient record, e.g., Significant Events or Orders, view or edit prior entries in the database in these categories, and add additional documentation for that category. The documentation is written or pushed to two areas of the database, one devoted to patient documentation and a second area corresponding to the selected category, e.g., Orders. The method and apparatus improves workflow efficiency and promotes a smooth transition from the thought process of the clinician to the ordering or prescription process, without the need for changing venues or screen displays.

20 Claims, 13 Drawing Sheets

(56) References Cited

U.S. PATENT DOCUMENTS

| | | | |
|---|---|---|---|
| 6,697,765 B2 * | 2/2004 | Kuth | 702/188 |
| 6,714,913 B2 * | 3/2004 | Brandt et al. | 705/2 |
| 6,829,604 B1 * | 12/2004 | Tifft | 707/707 |
| 6,915,254 B1 * | 7/2005 | Heinze et al. | 704/9 |
| 2003/0140044 A1 * | 7/2003 | Mok et al. | 707/10 |
| 2004/0078231 A1 * | 4/2004 | Wilkes et al. | 705/2 |
| 2004/0139092 A1 * | 7/2004 | Jones et al. | 707/100 |
| 2004/0243545 A1 * | 12/2004 | Boone et al. | 707/2 |

* cited by examiner

Fig. 3B

Stallman, Richard M - Structured Notes Entry Dialog

Interdisciplinary Patient Database: Structured Notes

Authored: ● Now ○ Date  Time:
Authored By: ● Me ○ Other  Source:
Co-Signatures: □ Incomplete □ Results Pending  Modify Template
Mark Note As: □ Priority

- Patient Information
- Family Contact Person
- Allergies
- Lab Results
- Other Results
- Nutrition
- Education
- Care Providers
- Orders
- Significant Events
- Outpatient Prescription Profile
- Health Issue

Problem List

| Problem | Coded Name | Onset Date | Type | Status | Text | Code | Coding System | History |
|---|---|---|---|---|---|---|---|---|
| ☑ Shortness of Breath | | 13-May-2005 | Admitting | Active | | | | |
| ☑ RO pneumonia | | 13-May-2005 | Admitting | Active | | | | |

Auto Enter
Section | Document

Review | Submit | Cancel
Copy Forward | Calculate 70
72
76A
76B
74
76
78

Fig. 4

Review/Preview

Review/Preview Structured Note

Orders
    Order - Laboratory; CBC; 09-Jan-2001; Corrected Results
    Order - Laboratory; PT; 21-Feb-2005; 1 or more Final Results Received
    Order - Laboratory; Electrolytes; 23-Feb-2005; 1 or more Final Results Recieved

Significant Events
    Significant Event - Immunization; Oral Polio; 3; Active
    Significant Event - Surgical History; Appendectomy; 3; Active

Health Issue
    Problem - Shortness of Breath; 13-May-2005; Admitting; Active
    Problem - RO pneumonia; 13-May-2005; Admitting; Active

Signatures
Guest (Physician)
    Author: - Orders, Significant Events, Health Issue
    Entered: - Orders, Significant Events, Health Issue

Health Issues Details - Alpha, 425 -- Web Page Dialog

Health Issue Details

Type: [*] ▼    Status: [Active] ▼    Scope: [This Chart]

Coding Scheme: [_____] ▼
Code: [_____]
Name: [_____]    [Search]
Short Name: [*_____]
Description: [_____]

Onset Date:  ● M/Y  [____] / [____]
             ○ Full Date  [____] 🗓

Expected Resolution: [_____] 🗓
Closed: [_____]

[Add New]  [Apply]

Entered: [_____]
Last Modified: [_____]

[OK]  [Cancel]  [Delete]

Review/Preview

Review/Preview Structured Note

Chief Complaint
    Chief Complaint
        Presenting symptoms - throat discomfort/pain  sinus pain

Past Medical History
    Past History
        Medical History - mastoid disease acoustic neuroma
        Malignancies diagnosed - lymphoma

Social History
    Occupation / Lifestyle
        Occupational History - dairy farmers
        Other relevant history - student
        Smoking
        Passive Smoking Exposure - yes

Review of Systems
    Eyes
        Ophthalmologic - positive
        Ophthalmologic Symptoms - photophobia
        Blurred vision - L
    ENT
        Mouth - decreased taste tongue ulcers

Physical Exam
    General Appearance
        General Appearance - abnormal
        Abnormal findings - diaphoretic pallid
    ENT
        Ears (External) - normal no lesions or deformities
        Ears (Otoscopic) - canals clear, tympanic membranes intact with good movement, no fluid
        Ears (Hearing) - grossly intact
        Nose (External) - normal, no lesions or deformities
        Nose (Internal) - abnormal
        Abnormal findings - deviated septum
        Mouth - abnormal
        Abnormal findings - gingival hypertrophy
        Pharynx - tongue normal, posterior pharynx without erythema or exudate

Significant events
    Significant Event - Oral Polio
    Significant Event - Diabetes Mellitus

Signatures
Taylor, Kari (Physician)
    Author: - Chief Complaint, Past Medical History, Social History, Reviews of Systems, Physical Exam, Significant events
    Entered: - Chief Complaint, Past Medical History, Social History, Reviews of Systems, Physical Exam, Significant events

ELECTRONIC PATIENT RECORD DOCUMENTATION WITH PUSH AND PULL OF DATA TO AND FROM DATABASE

CROSS-REFERENCE TO RELATED APPLICATION

The present application is a U.S. continuation patent application of, and claims priority under 35 U.S.C. §120 to, U.S. nonprovisional patent application Ser. No. 11/142,060, filed May 31, 2005, which patent application and any patent application publications thereof and patents issuing therefrom are hereby incorporated by reference herein.

BACKGROUND

1. Field

This invention relates generally to the field of computerized medical records management systems, and in particular to medical records software wherein patient record information is stored in electronic form in a database and made available to users such as physicians, nurses and hospital staff using a graphical user interface of a general purpose computer or workstation.

2. Description of Related Art

In the medical arena, hand written patient record keeping systems have evolved through many years of careful refinement and enhancement into systems which maintain a detailed manual record of medical information concerning each patient. To meet the needs of different hospital entities (such as doctors, nurses, pharmacy, accounting, laboratory, etc.) a manual record keeping system often requires that one piece of information be entered into multiple records. In addition it often requires that the same information that has not changed from visit to visit (such as family/social history, allergies, immunization status) be re-asked of the patient and re-documented in the current record. In certain instances, such as in the Emergency Department, this information may be asked and recorded as many as three separate times (on the Triage Note; the main ED record; and MD documentation) leaving the patient to wonder if there is any communication between healthcare providers and frustrating those healthcare providers who must fill out more and more paperwork. If the patient is admitted, this same information is then asked and recorded again by the admitting nurse and attending physician.

In a typical manual patient record keeping system a patient chart, usually in the form of a notebook, is maintained at the nursing station for each patient. The notebook is divided into a plurality of individual tabbed sections, such as Physicians Orders, Kardex, Nursing Care Plan, Nursing Assessment, and Laboratory.

Each of the above sections is further subdivided into a number of forms. The forms are those which are appropriate to the individual patient and/or such patient's physician. For example, within the Laboratory section there may appear forms for chemistry, hematology, blood gas, and microbiology.

In addition, a "flowsheet" chart is usually kept at the patient's bedside, particularly in a critical care environment. On the "flowsheet" chart there are individual areas for medication records, vital signs, intake/output, laboratory results, and other categories which are dependent upon the patient's affliction, such as intravenous (IV) drips.

Referring in particular to nursing functions, annotations to charts and/or nursing progress notes are made manually. Typically, brief notations are jotted down in various places through-out a shift. Sometime during the shift, typically at the end, the nurse makes a full notation into the nursing progress notes based on the brief notations or remembered items. This process can be very inefficient since notations may be forgotten or not copied appropriately. In particular, documentation and entry of physician orders, prescriptions and other activity has been viewed as two separate activities or steps, one step completing the documentation and a second step of entry of the order or prescription in the medical records of the patient.

The need for more efficiency of workflow and coordination between multiple departments and healthcare providers in a hospital environment has led to the advent of computerized medical records applications. Medical records management systems are known in the art and include the systems disclosed in the following U.S. Pat. Nos. 5,325,478; 5,247,611; 5,077,666; 5,072,383 and 5,253,362 all assigned to the assignee of this invention, and have been commercialized by the Assignee of this invention and others. The content of the above referenced patents are incorporated by reference herein. However, these and other systems would benefit for a more intuitive, efficient and streamlined method for adding documentation to a patient record. In particular, clinical documentation, whether automated (computerized) or manual (paper based), needs to reflect the thought process that a physician or nurse goes through as they are assessing and making plans for how to treat and care for patients. The present inventors have appreciated that during the thought process, and the documentation of the information obtained from the patient or family and of the decisions being made, the clinician ought to be able to initiate care plans, or orders, review previous data (e.g., lab results, vital signs, outpatient medications, allergies) without having to interrupt their workflow to fill out and or search through various separate paper forms, or paper charts, and without having to navigate out of or otherwise be disrupted from the documentation process. Aspects of this disclosure address this need.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments one or more of the above-described problems have been reduced or eliminated, while other embodiments are directed to other improvements.

In a first aspect, a computerized medical records system and apparatus is provided that can "push" or add clinical information to a database containing an electronic patient record, both in a documentation field of the database as well as a second field of the database corresponding to a separate category of the patient medical record. For example, while creating and entering documentation for the patient, the information created for the document (such as a new order) is simultaneously written to both the documentation field and to an Order field of the database. The physician's internal analysis of the information being documented might lead him or her to require documentation of a new order by the physician. This order can be simultaneously written to both the documentation field and the order field of the database.

Additionally, the system and method provide for a "pull" of information from the database containing data from an electronic patient record, such as Past Medical History, Current Medications, Vital signs, Lab Results, Allergies previously documented, etc., without leaving the documentation entry process. The push and pull of data to and from the database occurs during the documentation process and without the user having to navigate out of a document creation user interface into a separate interface or application, e.g., one for writing orders. The user can thus in a single action or user interface event, both complete patient documentation and write orders, order new prescriptions, note additional significant events, and take other action in other categories of the patient record. Heretofore, these were separately treated as multi-step processes.

Additionally, the user is able to "pull" information that was documented elsewhere—either in a previous visit or from the current visit. For example, information in the electronic patient record, such as their Past Medical History or allergies, can be entered in the database only once (e.g., when the patient is first admitted to the hospital) and it remains stored in a persistent fashion in the database. Such information, which may be termed a "longitudinal record" is thereafter available to practitioners when they later access the electronic patient record, e.g., when the patient comes in for a subsequent visit. Heretofore, inspection of the patient's prior medical history, etc. used to require looking at other forms in the current chart to find this data, or ordering the "old chart" from a medical records repository and searching for this same information. It was a very time consuming and redundant process.

Because this information in the electronic patient record is comprehensive and pulled from all the relevant areas (lab results, patient medical history and other information from an admitting interview, nurse's observations, orders from prior visits, etc.), it prevents the physician, for example, from ordering duplicate tests since the current orders are viewable at the workstation; it also prevents redundant documentation on multiple forms since once the information is stored in the database it is accessible on multiple forms in multiple places, i.e., at every workstation in the medical facility.

The preferred embodiments have further advantages in that they provide for efficiency and a smooth transition from the thought process to the ordering and documentation process, without the need for the user to change the user interface venue. The workflow of each user of a note containing the documentation is greatly streamlined. The clinician's documentation of the note is comprehensive and accurate as a result.

In another aspect, a medical records information apparatus for use with a database storing patient data is provided. The apparatus is in the form of an application (software) comprising a set of machine readable code stored on a machine readable medium and executable on a workstation. The application may take the form of a document or note creation application for use by a clinician such as a doctor or nurse. The application provides a user interface for display of data regarding a patient and entry of documentation by a user. The software (code) pulls data from an electronic patient record from the database for inclusion into the display of documentation as well as allows for entry of new documentation, e.g., writing new orders.

Furthermore, the entry of new documentation is pushed to a first location in the database devoted to documentation regarding the patient and to a second location in the database devoted to a predetermined category of an electronic patient record for the patient other than documentation regarding the patient. The categories of the patient record that are associated with the second location in the database may be defined by a system administrator or by the user, and may for example one or more of the following categories: Health Issues (e.g., symptoms, diagnoses, etc.), Past Medical History, Outpatient Medications, Prescriptions, Orders, Care Providers (e.g., a list of general practitioners and specialists or clinics assigned to the patient), Significant Events (e.g. prior surgeries, heat attacks, previous injuries or treatments, etc.), Allergies (e.g., allergies to drugs, allergies to foods or environmental factors), Patient Problems; Medication Profile; Flowsheet Observations, Lab Results, and Other Diagnostic Results.

In one embodiment, the pull of patient data from the database comprises the pull of one or more rows of data from the database. Each row of data in the database may be devoted to a specific entry in the category (e.g., a specific order for the patient in the Order category, a specific prescription that was given to the patient in the Prescription category, a specific lab test result in the Lab Result). Often, a multitude (3 or more) of rows of data will be returned to user interface for display. For example, if the patient is adding documentation regarding a new order, the user's selection of the order category to enter documentation on the user interface will be accompanied by a pull of all currently active orders for the patient in the medical record, and may for example consist of a dozen or more orders. In a preferred embodiment, each order is listed as a separate row on a grid or field of the user interface display, signifying a prior separate order for the patient. The user can select one or more orders for display in a structured note. If they wish, they can navigate back to the display of the pulled orders and then click on an icon and write a new order.

Another important aspect of the preferred embodiments of this invention is that the user is able to make a determination of which "pulled" elements become part of the current note or documentation, such as for example by clicking a box next to the pulled element(s) on the screen display and then clicking a "review note" icon, whereupon a window appears that displays the selected elements. As another example, the user may select a particular medication in a pull of current medications and click a "verify" icon, whereupon a documentation screen is displayed and the user can update medication information from the previous visit, rather than ask the patient to list all of their current medications. If a "pulled" medication is no longer active, the clinician does not select it from the display of all medication and it does not get added to this particular note. In addition, if the patient is taking a new over-the-counter or prescription medication, the clinician can enter that medication into the document. The application then automatically "pushes" the new medication data to the database area for current medications and to the documentation area, and thus is available to all healthcare providers from that point forward when they access the electronic patient record. The integration of documentation and the ordering of new medication is combined into a single user interface event.

In still another aspect, a method is provided for storing information regarding a patient in a database, comprising the steps of: a) presenting a user interface on a computing platform for entry of documentation for a patient, b) pulling at least one row of data from the database comprising a portion of an electronic patient record for the patient and presenting, at least in part, the row of data on the user interface; c) providing tools for entry of documentation from a user via the user interface, and d) pushing the entry of documentation to the database, and wherein the entry of documentation is pushed to a first area of the database devoted to documentation regarding the patient and to a second location in the database devoted to a predetermined category of an electronic patient record for the patient (e.g., Orders, Prescriptions, Significant Events) other than documentation regarding the patient.

In still another aspect, a medical records information system is provided comprising: a database storing patient data, and at least one computing platform operatively connected to the database and providing a workstation for obtaining data in an electronic patient record stored in the database and for writing new documentation to the database. The computing platform providing the workstation comprises a processing unit (e.g., personal computer CPU) a display device (e.g., screen) and a memory (which may be local to the device or on a shared resource) storing machine readable instructions for execution by the processing unit. The instructions provide a user interface on the display device for the workstation for display of documentation regarding a patient and entry of documentation by a user. The instructions pull patient data from the database for inclusion into the display of documentation on the user interface as well as allow for entry of new documentation. The entry of new documentation via the user interface is pushed to a first location in the database devoted to documentation regarding the patient and to a second location in the database devoted to a predetermined category of an electronic patient record for the patient other than documentation regarding the patient.

The nature of the overall architecture of the medial records system, and possible inclusion of other functionality in the system, is not important. A representative example architecture will be provided in the following detailed description by way of example and not limitation.

In addition to the exemplary aspects and embodiments described above, further aspects and embodiments will become apparent by reference to the drawings and by study of the following detailed descriptions. Moreover, the exemplary embodiment will be described in conjunction with representative and non-limiting examples of user interfaces to carry out the disclosed methods and as examples of a representative application, documentation entry user interface and medical record system. Persons skilled in the art will recognize that variation from the specifics of the disclosed embodiments and user interface design is possible without departure from the teachings herein.

BRIEF DESCRIPTION OF THE DRAWINGS

Exemplary embodiments are illustrated in referenced figures of the drawings. It is intended that the embodiments and figures disclosed herein are to be considered illustrative rather than restrictive

FIG. 3B is a screen shot of a problem list showing problems pulled from the database and presented to the user as part of documentation process.

FIG. 4 is a structured note that appears on the display after selection of problems from the display of FIG. 3B and the user activates the "review note" icon. The structured note includes rows of data pulled from the database in the fields Orders, Significant Events, Health Issues and Signatures.

FIG. 5 is a screen shot showing a display wherein a user can add new health issues and have a new entry written to the database.

FIG. 6 is a screen shot showing significant events pulled from the database and presented as part of a documentation process.

FIG. 7 is a screen shot showing a dialog box wherein a user can add new significant events.

FIG. 8 is structured note showing selected items returned from the database as part of the note, including the selected Significant Events from FIG. 6.

FIG. 9 is a screen shot of a flow sheet from an electronic patient record as part of a documentation process, in which the user can select particular elements from the screen shot for inclusion in a note or document.

FIG. 10 is a screen shot showing an electronic patient record; the display shows where a nurse or other user would enter data into the flow sheet.

FIG. 11 is a screen shot of a lab results from an electronic patient record displayed as part of a documentation process, wherein the user can select particular lab results to pull into a note or document.

FIG. 12 is a screen shot of orders from an electronic patient record displayed as part of a documentation process, wherein the user can select particular orders to pull into a note or document.

DETAILED DESCRIPTION

A. Overview

Figure 1:
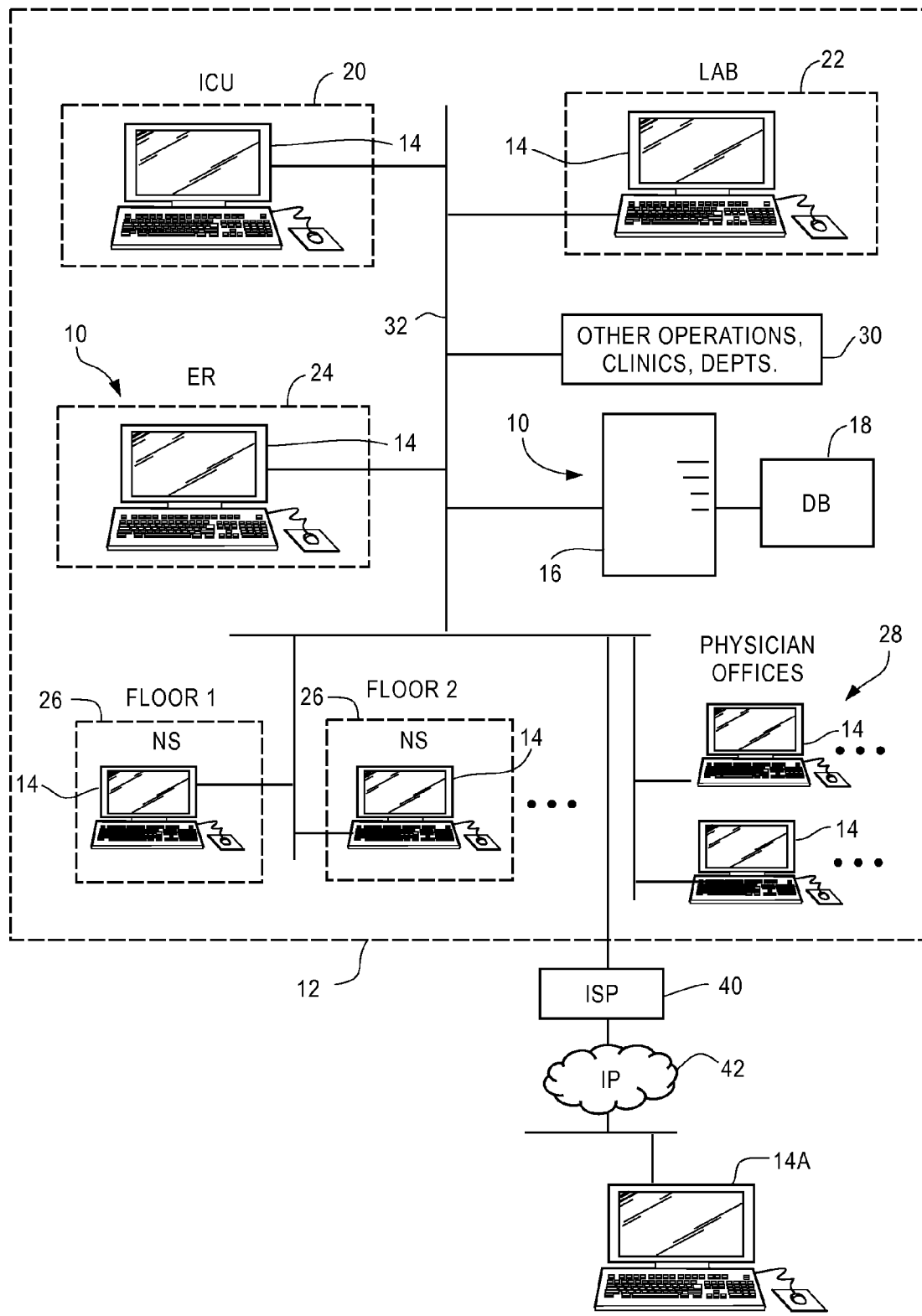
FIG. 1 is a block diagram of a computerized medical records system for a plurality of patients served in a medical facility. The system includes the push/pull features of this invention and optionally additional features not relevant to the present discussion.

Referring now to FIG. 1, a representative and non-limiting example of an environment in which the invention can be practiced is shown in block diagram format. In particular, FIG. 1 depicts a computerized medical records system 10 that is used by clinicians (physicians, nurses and other medical personnel). The system is shown installed in a medical facility 12 indicated in dashed lines. The medical facility may for example be a hospital, nursing home, clinic, or other medical enterprise. The details on the medical enterprise and type of health care services is not particularly important. A primary application of this invention is in the hospital environment, and therefore the following description will be made in conjunction with a hospital.

The medical records system 10 includes a plurality of distributed workstations or client computers 14, a central database server 16 (e.g., Oracle 9i database server) and a database 18 containing electronic patient records. The workstations 14 could be for example general purpose computers with a processing unit and graphical display unit. The workstations 14 could also be hand-held computers. The workstations 14 include a memory storing an interactive, client-server based patient documentation application that is executed by the processor in the workstation. The application provides user interface tools in the form of graphical screen displays which allow the user access the electronic patient records stored in the database and add clinical documentation regarding a patient being treated at the facility 12.

As shown in FIG. 1, the facility 12 may include an Intensive Care Unit 20 with a workstation 14, which may be used by ICU physicians and ICU nurses to access patient records and input orders, write prescriptions, view patient allergies, and input documentation. The facility may also include one or more laboratories 22, each of which may include a workstation. Lab personnel may input test results into the patient record stored in the database 18. The facility may also include an Emergency Room (ER) 24, where a workstation 14 is provided for ER clinicians to records and input orders, write prescriptions, view patient allergies, note significant events and chief complaints of the patients and input them into the electronic patient record stored in the database 18. The facility may also have a number of patient rooms and provide nurses stations (NS) 26 on each floor, each of which has a workstation 14. Additionally, physicians' offices 28 may also include workstations 14, in the form of personal computers. The facility 12 may have other operations, clinics, departments, etc. as indicated at 30, each of which may be provided with additional workstations. The workstation are networked on a local area network 32 wherein all of the workstations may exchange data with the central database server 16 and thereby access the patient records stored in the database 18 and write documentation and orders, prescriptions, and other information to the database 18.

The network 32 may include a router (not shown) providing a connection to an internet service provider (ISP) 40 providing access to an external wide area internet protocol network 42 such as the Internet 42. A workstation 14A may be coupled to the enterprise network 32 via the ISP 40 whereby a clinician authorized to access patient records in the database 12 may do so via the Internet 42, ISP 40 network access server and local area network 32. Thus, a workstation 14, 14A creating patient documentation need not necessarily physically reside on the network 32 or be physically located within or at the enterprise 12.

Thus, the medical records system 10 that is installed in the medical facility 12 allows clinicians to access patient records in a database 18. The system 10 may take the form of a hospital medical records information system, and such systems are generally known in the art and commercially available from Eclipsys Corporation, Siemens, and others. The preferred embodiment of such a system provides clinicians information they need, when and where they need it—at the point of care (e.g., in the ER or at the nursing stations 26), in the offices 28, even at home via a computer 14A and the Internet 42.

Figure 2:
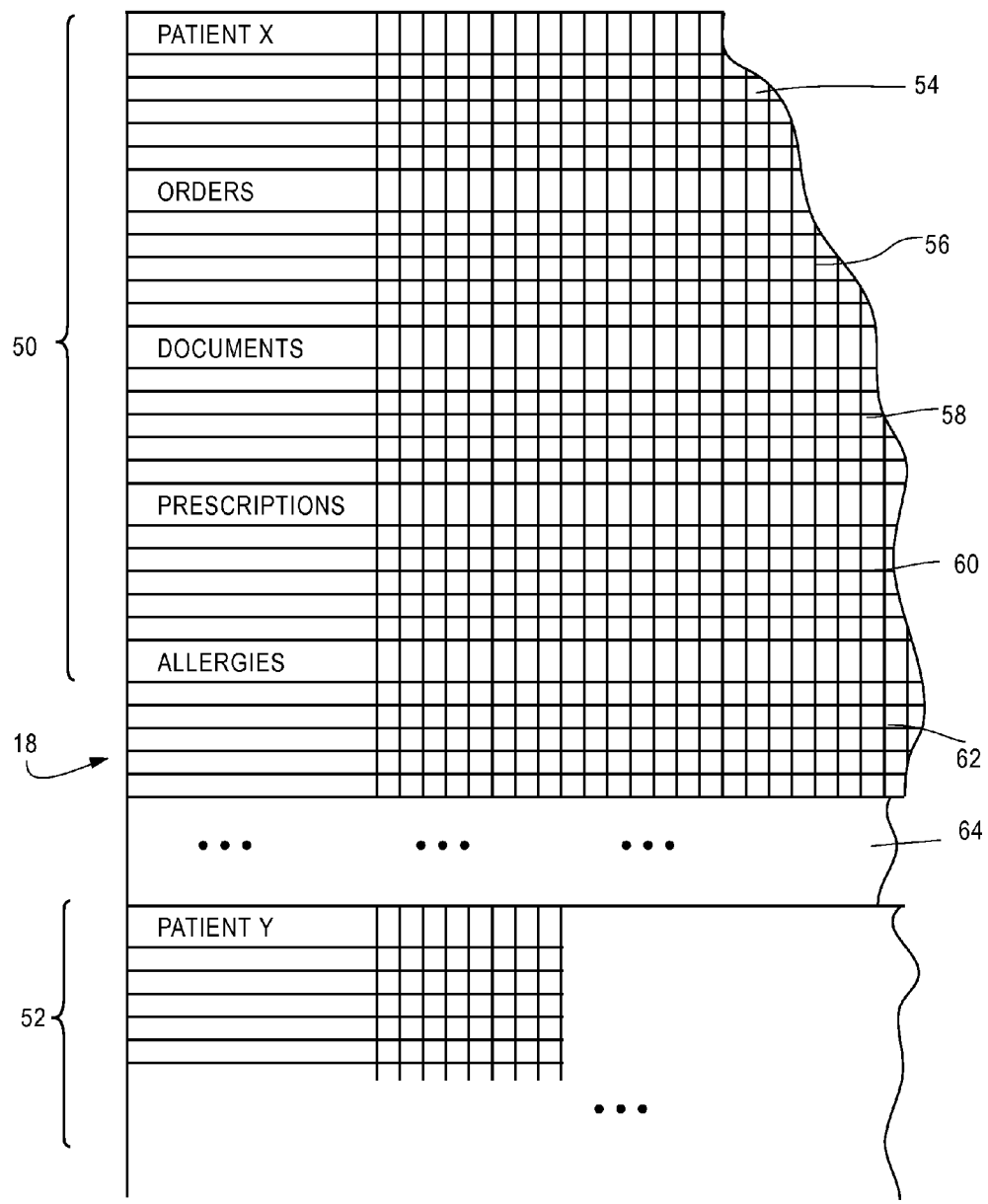
FIG. 2 is a schematic representation of the database of FIG. 1, showing an electronic patient record for patient X, with the recording including a number of fields or categories, each associated with a different portion of the database record. These categories, which may be user or customer defined, include categories such as Orders, Documents, Prescriptions, Allergies and still others. The illustration of FIG. 1 shows a relational database implementation wherein data is organized in rows and columns. However, the use of object-oriented database design in which data is stored as objects is an alternative implementation and considered to be within the scope of this disclosure.

A schematic representation of the database 18 is shown in FIG. 2. The database includes a multitude of electronic patient records 50, 52 each comprising rows and columns of data. A first field 54 is shown directed to patient information, such as name, address, insurance carrier, date of birth, etc.

A second field 56 contains orders for the patient. The orders are determined by health care personnel treating the patient. Each row in the orders field 56 may constitute a specific order, and the various columns in the row devoted to different aspects of the order, such as the entering physician's name, the type of order, the date it was placed, etc.

A third field 58 is directed to documents (i.e., documentation) entered by a physician or nurse. Each row may represent specific instances of documentation created by a user.

A fourth field 60 contains prescription medications ordered for the patient. A fifth field 62 contains data of all the patient's allergies. Other fields 64 are also present, and may include fields devoted to significant events, health issues, care providers and others. The name of the categories in the electronic patient record, and the number of categories is not particularly important and may vary depending on the environment and the choices made by a system administrator.

In a first aspect, a medical records information apparatus is disclosed for use with a database 18 storing patient data which provides for push and pull of data to and from the database 18 in conjunction with a medical records documentation process performed on a user interface of a workstation 14 or 14A. The apparatus comprises an application (software) comprising a set of machine readable code stored on a machine readable medium and executable on a workstation 14, 14A The application provides a user interface for display of data regarding a patient and entry of documentation by a user. Representative examples of the user interface are shown in FIG. 3 and subsequent figures. The code in the application pulls patient data from the database 18 for inclusion into the display of documentation, as well as allows for entry of new documentation by the user (typically a nurse or physician). The entry of new documentation is pushed to a first location in the database 18 devoted to documentation regarding the patient (location 58 in FIG. 2). The entry of new documentation is also pushed to a second location in the database devoted to a predetermined category of an electronic patient record (such as location 56, 60, or 62) for the patient other than documentation regarding the patient.

For example, consider an example of a physician entering documentation for a patient and in the process of documentation decides to enter a new order for the patient, such as ordering a new test. While creating and entering documentation for the patient, the information created for the document (such as a new order) is simultaneously written to both the documentation field or table 56 in the database and to an Order field or table 56 of the database. (Here, in this example, the "other predetermined category of the electronic patient record" is the Order category). This is an example of a "push" of data to the database as part of the entering of documentation to two areas of the database—the order area and the documentation area. The push of data can be to other categories of the electronic patient record, and the name or category can be configures by the system administrator. Examples of these categories include health issues, past medical history, outpatient medications, prescriptions, orders, care providers, significant events, allergies, patient problems, and flowsheet observations.

Additionally, the application provides for a "pull" of information from the database containing data from an electronic patient record, without leaving the documentation entry process. For example, while creating a note, the application pulls information of all prior (or current) orders from the patient, reading row by row the entries in a table in the Order section of the database for the electronic record for the patient. In a typical situation where a relational database is used the database for the electronic patient record, the data is typically stored in a plurality of tables, each table comprising rows and columns of data, such as shown in FIG. 2. Each row will typically be a separate order, prescription, significant event, or other entry in the category. Thus, in a preferred embodiment the pull of patient data from the database comprises the pull of one or more rows of data from the database. Representative embodiments of the application described herein display the data pulled from the database in a grid form, with one or more rows of information corresponding to one or more rows of data from the database.

In a preferred embodiment, the push and pull of data to and from the database occurs during the documentation process and without the user having to navigate out of a document creation user interface into a separate interface or venue (e.g., booting up a separate application and transitioning out of documentation and into a new application). The user can thus in a single action or user interface event, both complete patient documentation and, e.g., write orders or enter new significant events. The process works for other categories of a patient record, such as new prescriptions, note additional significant events, or make new findings or take other action in other categories of the patient record. Heretofore, these were separately treated as multi-step processes.

The invention has advantages in that it provides efficiency and a smooth transition from the thought process to the ordering process, without the need for the user to change the user interface venue. The workflow of each user of a note containing the documentation is greatly streamlined. The clinician's documentation of the note is comprehensive and accurate as a result.

As the data entered during the documentation process is pushed to the database, the relevant tables in the database (documentation and Orders, for example) are substantially immediately updated and stored in the database in a persistent manner. When other users of the hospital information system thereafter access the electronic patient, they access the most up to date information including the latest documentation and orders. In a typical embodiment, a medical records information system in accordance with the invention is installed at a medical enterprise 12 such as a hospital and the application as described herein is loaded on a plurality of workstations at the medical enterprise 12. For example, it may be loaded on all the physician office computers, nursing station workstations, on hand-held computers used by hospital personnel, and in each of the clinics and laboratories in the hospital, e.g., ICU, ER, X-ray LAB, Nuclear Medicine Lab, etc. Thus, all the care providers in the hospital have access to the electronic patient record in the database.

In a related aspect, a method is provided for storing information regarding a patient in a database. The method comprises the steps of:

a) presenting a user interface on a computing platform (e.g., workstation) for entry of documentation for a patient, b) pulling at least one row of data from the database comprising a portion of an electronic patient record for the patient and presenting, at least in part, the row of data on the user interface (See FIG. 3 and subsequent figures);

c) providing tools for entry of documentation from a user via the user interface (e.g., icons, spaces on the display and other tools), and d) pushing the entry of documentation to the database 18, and wherein the entry of documentation is pushed to a first area of the database 18 devoted to documentation regarding the patient (58) and to a second location in the database 18 devoted to a predetermined category of an electronic patient record for the patient other than documentation regarding the patient, such as location 62 or 56 in FIG. 2.

In one embodiment illustrated below, the method provides a user interface allowing a user to select from a menu or list of categories of data corresponding to a plurality of separate locations in the database (Orders, Significant Events, Allergies, etc.), a category for which to add documentation regarding the patient (e.g., Orders), and wherein the selection of the category (e.g., Orders) pulls one or more rows of data from the database into the user interface for display, at least in part on the user interface. For example, when the user selects Orders from a list displayed on the left hand side of the screen, all prior orders are returned from the database. The orders, one per row in the database, are displayed on the database. The entry of documentation regarding the category is pushed to both the portion of the database directed to documentation and to the location in the database directed to the selected category. Thus, for example when the user selects ORDERS, the entry of data at the user interface (a new order) is pushed to a documentation area of the database for the patient and an order area of an electronic patient record for the patient in the database.

In a typical embodiment, the method is implemented in software at a workstation 14 or 14A, and wherein the method of entering documentation and pushing to separate areas of the database is available at each of the workstation in the enterprise. The method is thus performed in parallel by a plurality or workstation in a medical enterprise. The database is substantially immediately updated each time new entries are written to the database, so that each user accessing the electronic patient record is reviewing the most up to date information.

In still another aspect, a medical records information system 10 is provided comprising a database 18 storing patient data and at least one computing platform o workstation 14, 14A operatively connected to the database 18 (via the network 32 and database server 16). The workstation is provisioned with software for obtaining data in and electronic patient record stored in the database and for writing new documentation to the database. In particular, the workstation 14 includes a processing unit (CPU, e.g., Intel Pentium processor), a display device, and a memory (e.g., hard disk) storing machine readable instructions for execution by the processing unit, wherein the instructions provide a user interface on the display device for the workstation for display of documentation regarding a patient and entry of documentation by a user.

The instructions pulls patient data from the database for inclusion into the display of documentation on the user interface as well as allows for entry of new documentation, and the entry of new documentation via the user interface is pushed to a first location in the database 18 devoted to documentation regarding the patient and to a second location in the database 18 devoted to a predetermined category of an electronic patient record for the patient other than documentation regarding the patient.

B. Exemplary Documentation Application and Method with Push and Pull to Database With the above overview in mind, several examples of push and pull of data to and from a database in conjunction with a medical records documentation application will now be described in conjunction with FIGS. 3-12.

Figure 3A:
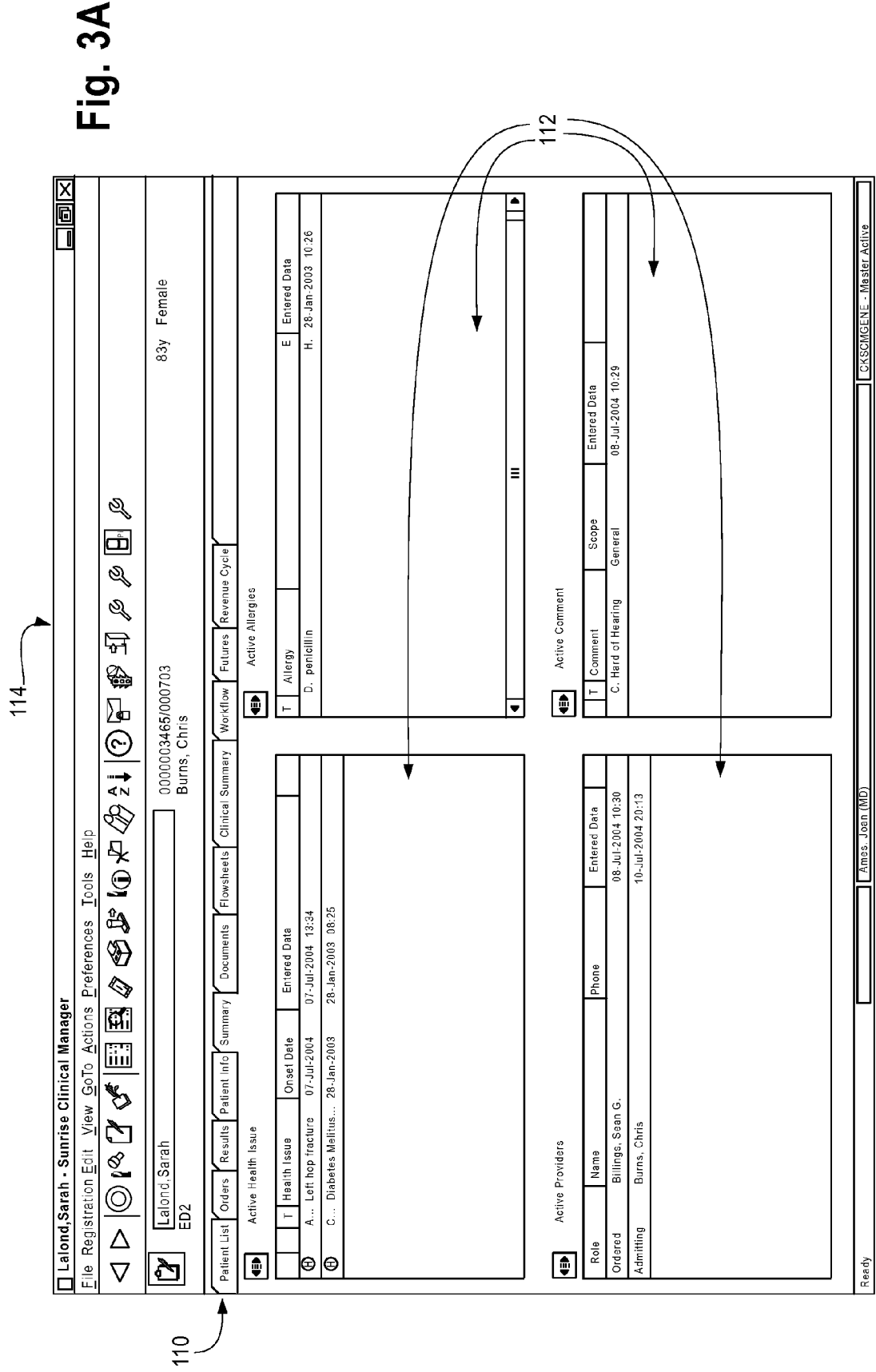
FIG. 3A is a screen shot showing an electronic patient record retrieved from the database of FIG. 2 and displayed on workstation of FIG. 1.

FIG. 3A shows a display of an electronic patient record stored in the database 18, presented on a screen display of a workstation 14. The display includes a series of tabs 110, wherein patient data is stored in different fields of the database corresponding to different categories of patient data. These tabs include, from left to right, Patient List, Orders, Results, Patient Info, Summary, Documents, Flow Sheets, Clinical Summary, Workflow, Futures, and Revenue Cycle. The name and type of categories is of course not critical and can be user defined. The user has clicked on the Summary tab and the four panes 112 appear, showing active health issues, active allergies, active providers and active comments. If the user were to begin the process of adding documentation but without the new functionality to be described below, the user would select a document icon from the icons 114 at the top, start writing their note, close it, navigate back to this screen, go back to this screen, and so forth. With the push and pull functionality to be described below, the user is able to select data from the patient record and bring it directly to the note without having to navigate back to a summary screen to view it.

FIG. 3B shows a user interface 70 presented on the screen of one of the workstations 14 in a clinical documentation application loaded on the workstation. The application includes instructions for presenting a screen display to the user and allowing the user to select a patient in which to enter documentation. The user is presented with the screen display of FIG. 3B. The user has clicked on an icon or otherwise made a selection that they wish to create a structured note (documentation) that includes one or more entries from a "problem list", which is a list of significant health issues for the patient. The left hand pane 72 shows a number of categories 74 of the electronic patient record, each one having an associated field in the database 18 as shown in FIG. 2.

When the user makes the selection of the "problem list" in pane 72, the application pulls from the database 18 all the rows of data in the problem list or Health Issues field in the database 18 for the patient. The rows of data are presented in the central pane 74 of the display, each specific problem in its own row. There are two rows 76, one row 76A containing a shortness of breath problem, and another row 76B devoted to RO pneumonia problem list. The user can select a box at the left hand edge of each row to select a health issue for which to add to a structured note, and then click on the review note icon 78.

All current problems in the display of FIG. 3B do not need to be selected for documentation, and just one may be selected. For example, if the patient also had a chronic problem with Hyperlipidemia (the display of FIG. 3B would include a third row of data regarding this problem), it may not be pertinent to the progress note the clinician is writing and therefore it would not be checked. However, it is pulled from the database and presented in the display of current Heath Issues.

FIG. 4 shows a display of a "structured note" user interface display wherein the application pulls all the data in the fields of the database for the patient corresponding to the orders, significant events, health issues ("problem lists") and authors of the data. The display of FIG. 4 can be presented in response to the clicking of the review note icon 78 in FIG. 3B. Note that the two health issues from FIG. 3B are presented in the note of FIG. 4, since the box next to each health issue was checked in FIG. 3B. When the user clicks the OK icon, the note is written to the documentation field of the database.

FIG. 5 shows a user interface display that appears when the user wishes to add a new health issues entry into the database for the patient. The user enters the information into the fields provided. All the information is pushed to a single row of data in the database in the documentation field, with the various information in the boxes being written to different columns. When the user clicks on OK, the data entered is written or "pushed" to a row in the documentation field (58, FIG. 2) and to new row in the field (64, FIG. 2) directed to health issues. Documentation of a new health issue occurs in one user interface event. The new health issue would then appear in the structured note of FIG. 3B if the user navigates back to the display of FIG. 3B and activates the "review note" icon.

Figure 6:
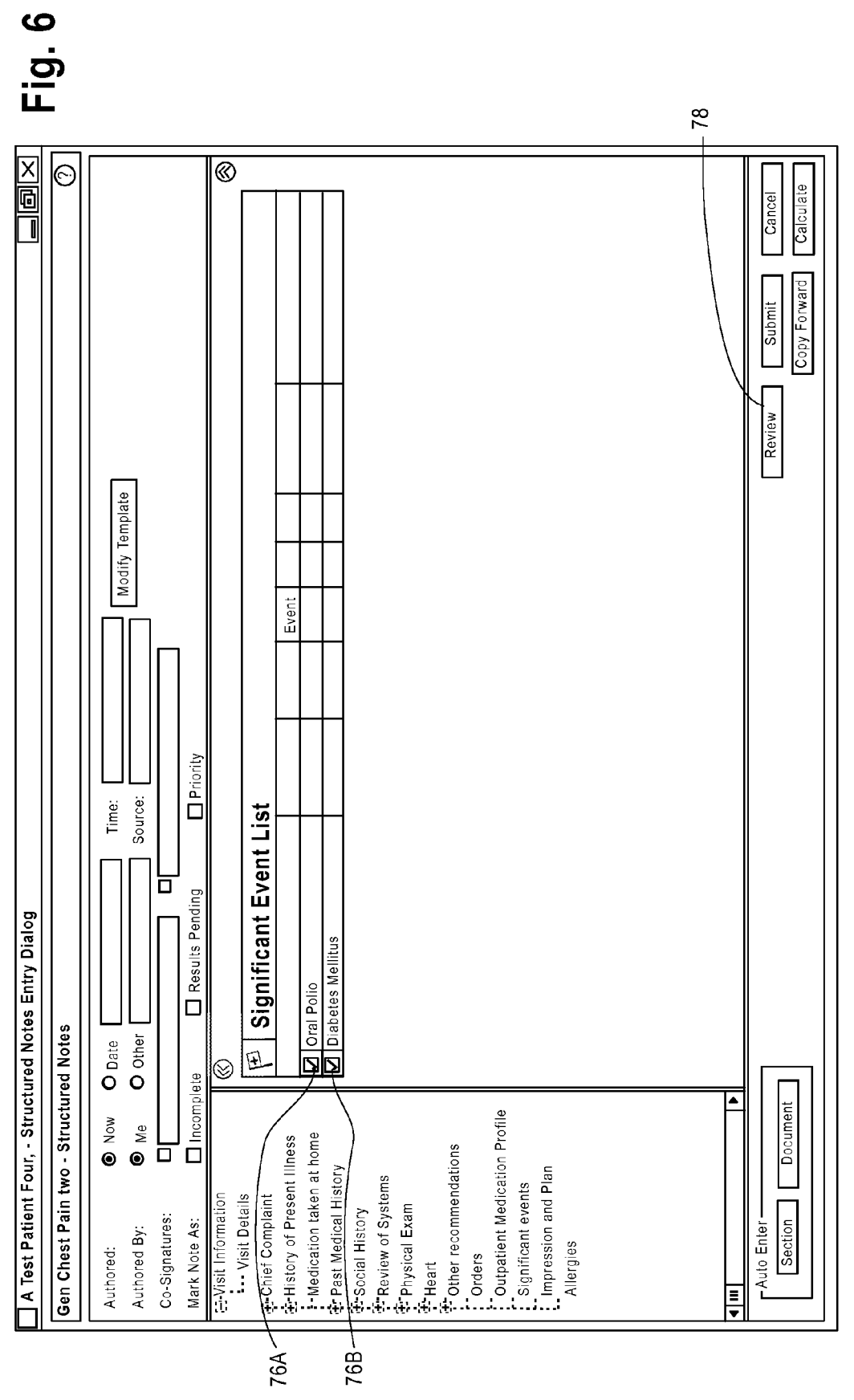

Referring back to FIG. 3B, consider the situation where the user wishes to add documentation regarding a Significant Event or include a significant event in a structured note. As noted above, the user interface provides a first display area 72 displaying categories of data corresponding to a plurality of separate locations in the database 18, including a Significant Events (third from the bottom). The selection of the categories pulls one or more rows of data from the database 18 into the user interface for display in a second display area corresponding to the selection of the category. As shown in FIG. 6, the selection of Significant Events causes the area 70 to show the significant events. There are two rows of data in this field which are pulled into the display. The left hand end of each row includes the box which the user can check (as shown) so that when they click on the document icon, the selected significant events are pulled into the documentation (structured note). When they are finished, the resulting note is pushed to the significant events and documentation fields of the database.

Figure 7:
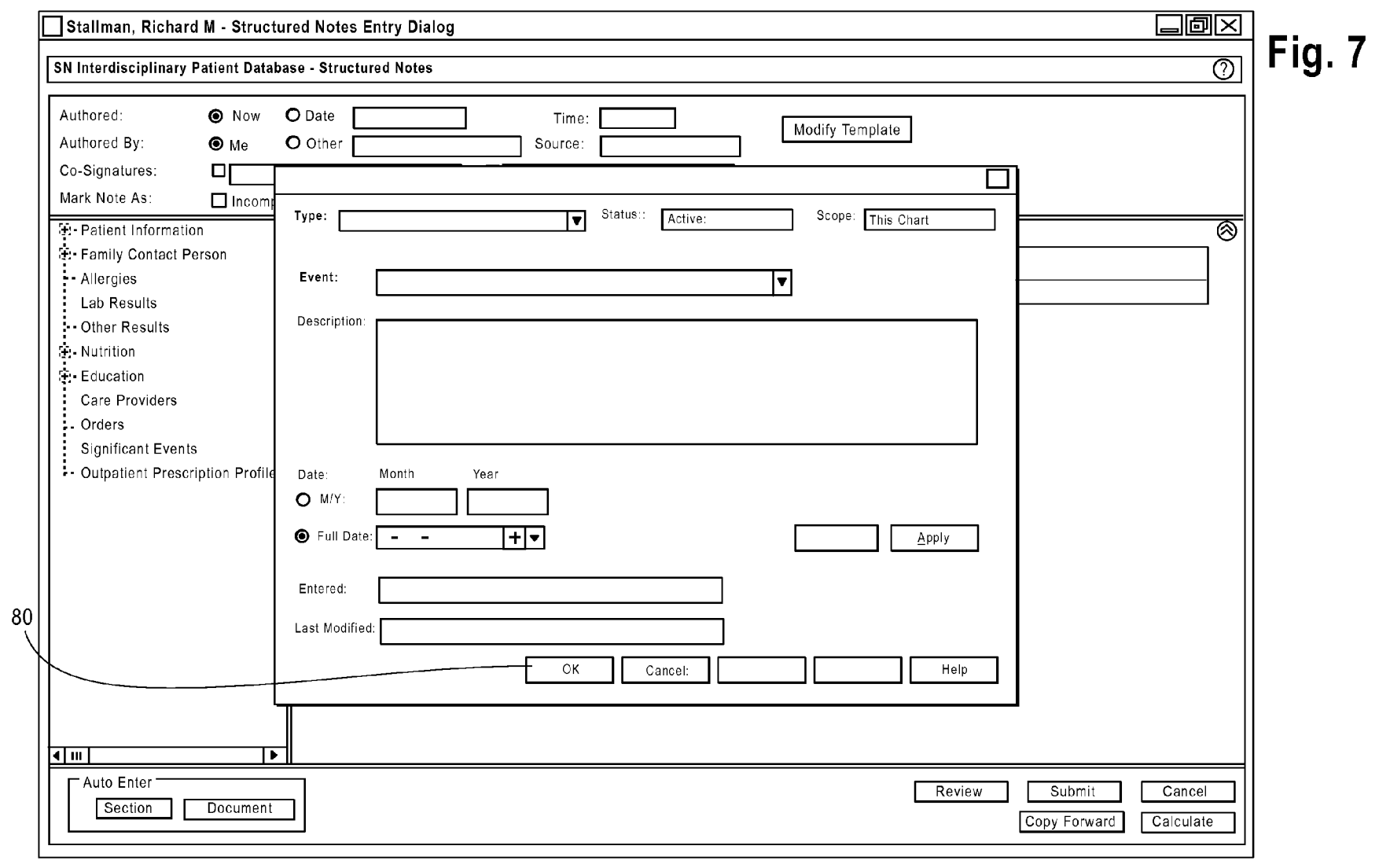

If they click on an "add new" icon in FIG. 6 (not shown), a dialog entry box appears as shown in FIG. 7. The user is presented with a dialog box to add documentation and other information regarding a new significant event for the patient. The user clicks on the OK icon 80 and the data is written to the documentation field and to the significant event field in the database.

FIG. 8 shows a display when a user navigates to a structured note for the patient after selection of various data from fields of the database for inclusion into the note. This display would appear when the user selects "review note". The note shows data from multiple fields pulled from the database and presented on the user interface, including the significant events of FIG. 7, Physical Examination, Review of Symptoms, and Past Medical History among others. Any newly created significant events will appear in the note of FIG. 8.

The process described for both pushing and pulling data from the database is similar for adding documentation regarding allergy information. The user selects this topic on the left hand pane and allergy data is pulled from the database and presented to the user. The user can add new documentation or note new allergies and this information is written to both the documentation and allergy fields of the database. A similar process occurs for Medication Profile, Orders, Care Providers, and other categories.

Flowsheet

Figure 9:
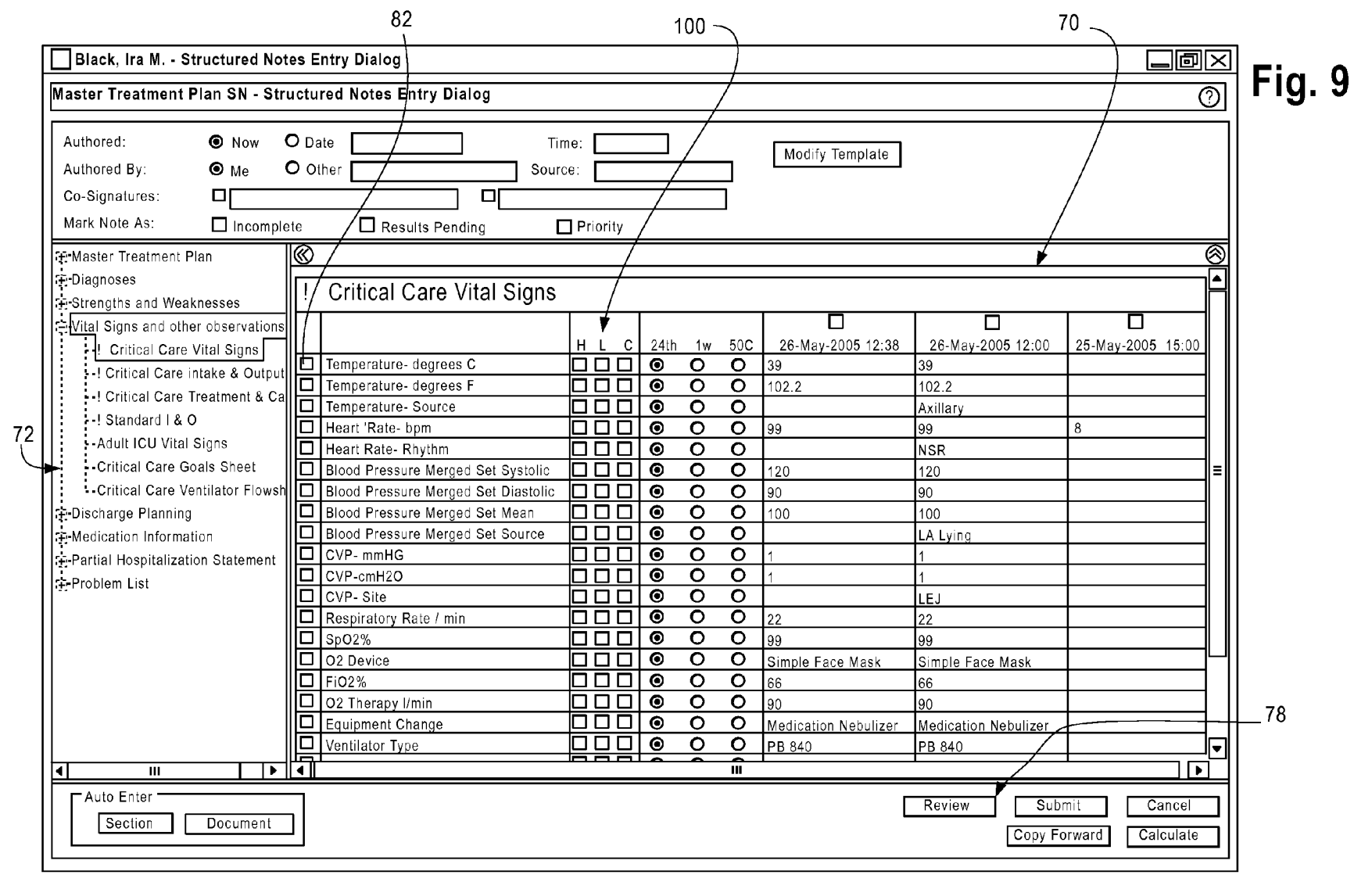

FIG. 9 is an example of a screen display of a flowsheet for a patient. The electronic flowsheet provides a convenient vehicle to summarize periodic clinical findings and is important to the note-writing process. The clinician may want to pull into a structured note actual data values from a specific point in time or may want to summarize highs, lows and means that occurred over a period of time. Because different environments will have different time frames in which data was stored (for example, the ICU may have every 5 minute vitals, where an Outpatient Clinic may have once a day or once a month)—there needs to be configurability per environment as to the display of the data.

As a general rule, the most recent set of data and/or the data within the last 24 hours is what is most important for the note. However, the clinician may want to summarize highs and lows or a trend, therefore additional data must be accessible. Each Environment defines which time frame is displayed when the Section (Flowsheet) is selected. For Inpatients, the default time frame is 24 hours (this can be further broken down by additionally defined environments). For Outpatients, the default time frame is 1 week.

In the pane 70, the user is presented with a list of clinical observations and several time periods over which the observations were collected. The user can select for inclusion into the documentation (structured note) the patient's temperature by checking a box 82 and clicking on the review note icon 78; a window appears and the user can enter documentation regarding temperature and the documentation is written to the database in the documentation and flow sheet fields in the database.

As another example, the user can click on the boxes 100 under the heading H, L, or C (for High, Low and Current) in a row for a parameter of interest, e.g., heart rate, and then click on "review note" 78 on the display. The user is then presented with structured note like FIG. 8 and the selected values from the database displayed in FIG. 9 are pulled into the note. When they are done and click "OK", the data is pushed to the documentation field and the flowsheet field of the database. Note further the grid layout of the flow sheet display in pane 70, each row being one row of data in the database.

As another example, the flowsheet display of FIG. 9 allows the user to select specific charted information (such as Temperature, Blood Pressure or other flowsheet data) and decide what information goes into a progress note (documentation being created). For example, the clinician can select Temperature—degrees F. by placing a checkmark next to that item on the left. Then, the patient can further cull the desired information by selecting H (highest value), L (lowest value) or C (current value) and the desired time frame for the search of this information. In this example, it is a 24 hour period, one week or since the start of the chart. The user then clicks on the review icon 78. The relevant data is pulled from the database, such as the highest temperature for the last 24 hours. This allows the clinician to quickly summarize clinical information that is pertinent to a progress note they are creating without having to review multiple flowsheets and columns of data created by the nurse. Only the pertinent data needs to be selected, and such data is selected by choice of boxes to check in the pane 72 of FIG. 9.

Figure 10:
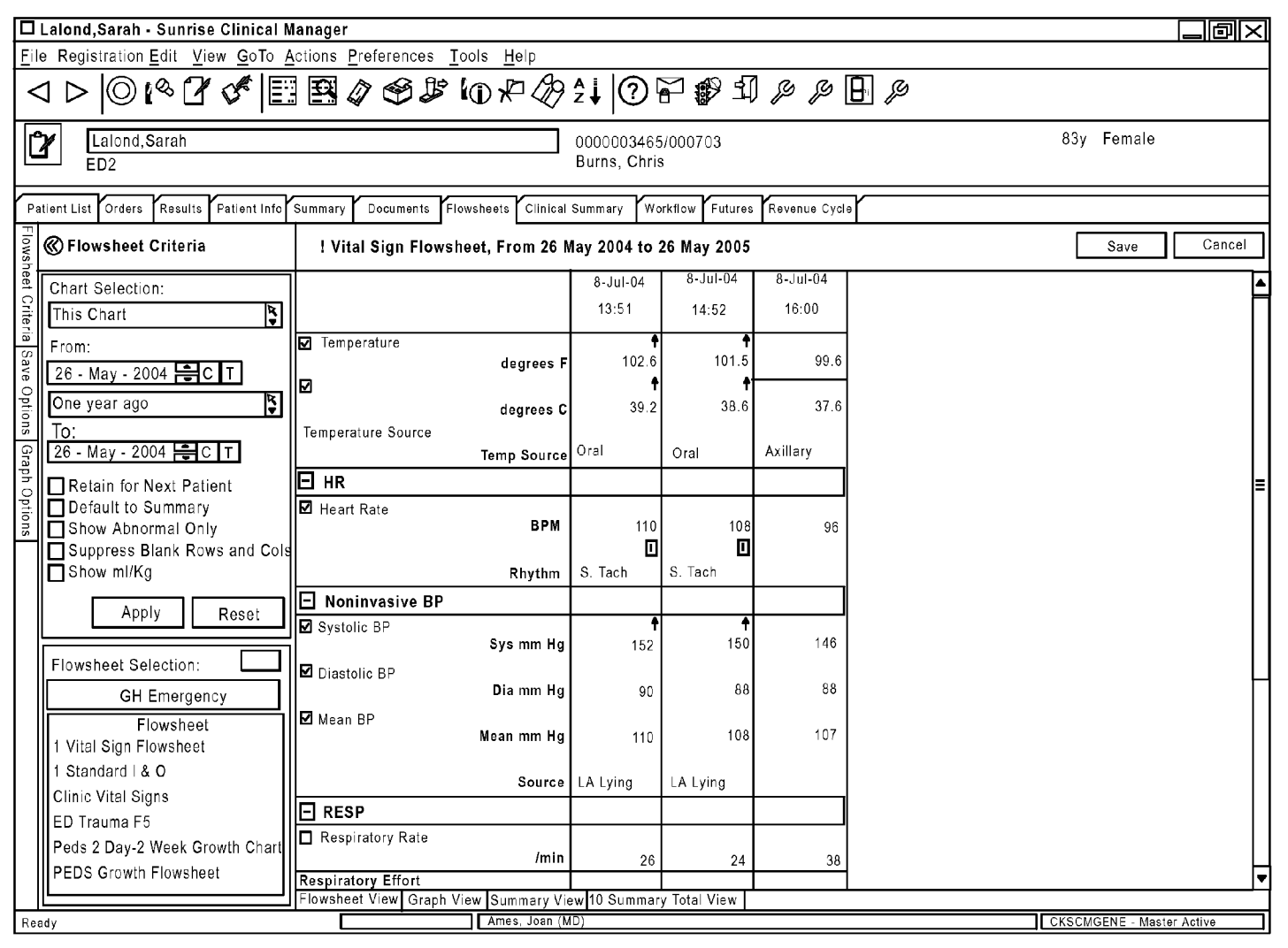

FIG. 10 is a screen shot which shows a typical flowsheet, in an environment where the information is entered and reviewed but without the push and pull functionality as described herein. The creation of a structured note using the pull feature is performed using the user interface display of FIG. 9.

Figure 11:
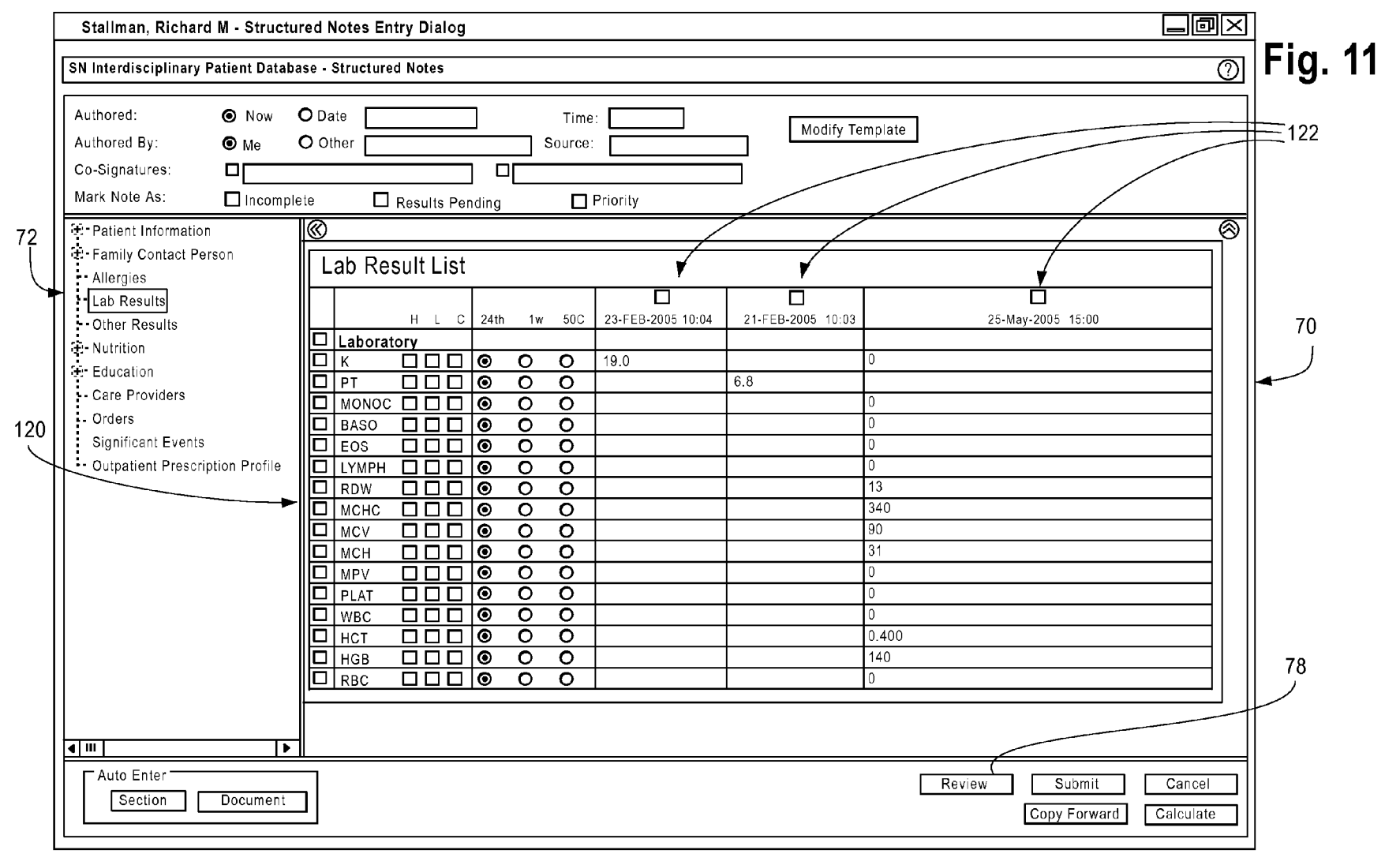

FIG. 11 is a screen shot of a lab results display, which appears when they select lab results in the left hand pane 72. The clinician is able to select pertinent lab results to add to a note in the same manner as in the other Figures—they check a box 120 on the left hand side of the main pane 70 and click on review note icon 78 and a presented with a progress note where they can add documentation. The documentation can then written to the database in both the lab results field and to the documentation field of the database. The value here is that often times the clinician feels the need to re-document these lab values even though they may be normal and/or are stored elsewhere in the chart. Without the functionality described herein, the process was laborious, redundant, and prone to errors in transcription. The push/pull functionality allows the clinician to quickly visualize relevant information, decide what is pertinent to the progress note, and "pull" the data (lab result of interest) from the database directly into the progress note. If desired, the entire set of lab values can be selected and pulled into the progress note with a single selection of the box 122 at the top of the relevant time column.

Figure 12:
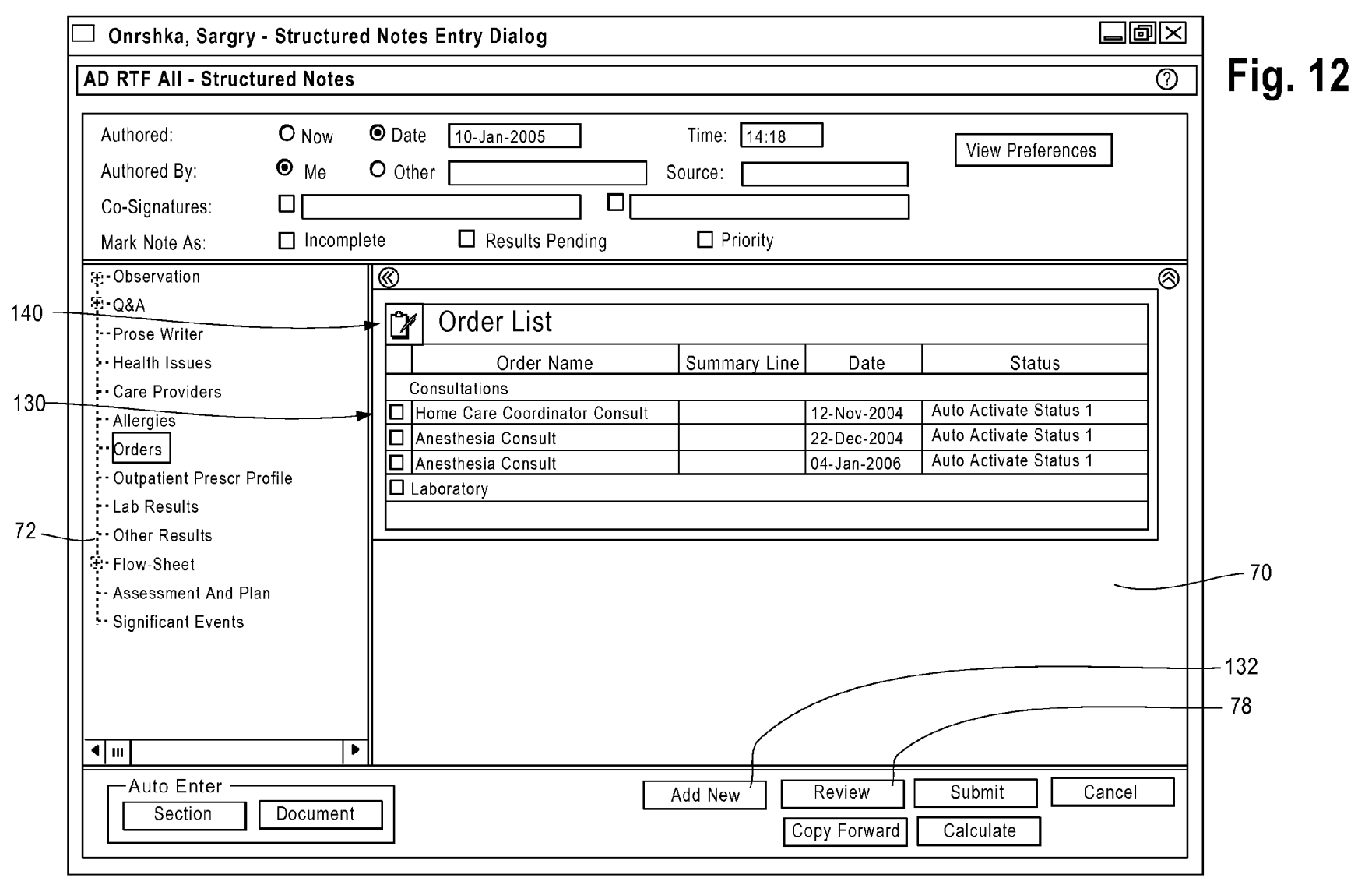

FIG. 12 is an example of an Orders documentation screen and appears when the user selects orders in pane 72. All current orders appear in pane 70, each row in the orders list corresponding to a row of data from the database. The user can select one or more orders to add documentation checking a box 130 and clicking the review icon 78, whereupon the selected orders are presented in a structured note (like FIGS. 4 and 8). When they are done, the note is then written to the database in the orders field and the documentation field. If the user clicks on the Add New icon 132, a dialog box appears and the user can enter new orders which are then written to the database in the orders field. As a user is documenting in a structured note, at any time they can for instance, add a new order, and have that order return to the body of the structured note (as in FIG. 8), without leaving the documentation entry process. They simply navigate to the display of FIG. 12 and click on the icon 140, whereon they are presented with a window for entry of a new order and this order then appears in the structured note (FIG. 8). This provides efficiency and smooth transition from the thought process to the ordering process without the need for changing user interface venues. The workflow for each clinical user of a note with a push/pull section is greatly streamlined. The clinician's documentation of the note is comprehensive and accurate as a result.

Optional features can be built into the disclosed medial records documentation application, or the documentation application may be incorporated into a larger hospital information system. As examples of such advanced features, as soon as a physician places an order, the application preferably transmits that order immediately, accurately and appropriately to all relevant caregivers. The Pharmacy, Lab or Radiology department can go to work immediately filling the order. Administering nurses know exactly what needs to happen and when. The physician's care plan is carried out efficiently and accurately. Patients' comprehensive medical records—encompassing every previous inpatient or outpatient encounter—are available whenever and wherever physicians need them. Physicians can electronically review and sign documents with a single click at their own convenience. Documentation is streamlined by discipline-specific content and flexible formatting that allows each physician to customize the screens according to his or her work patterns. Structured documentation tools as illustrated herein allow for rapid data entry and the generation of well organized, legible prose documents that can be thoroughly mined for data collection. All previously documented information can be carried forward (allergies, current medications, vital signs and past medical history) and "pulled in" to the documentation process, eliminating extensive manual chart review.

While a number of exemplary aspects and embodiments have been discussed above, those of skill in the art will recognize certain modifications, permutations, additions and sub-combinations thereof may be made to the specifics of the preceding disclosure. It is therefore intended that the following appended claims, and claims hereafter introduced, are interpreted to include all such modifications, permutations, additions and sub-combinations as are within their true spirit and scope.

We claim:

1. An information apparatus for use with a networked database, comprising:
    (a) a computing device having a processor and a machine readable medium containing machine readable code for performing a computer implemented method and executable by the processor of the computing device, the processor being configured to perform the implemented method,
    (b) wherein the computing device is configured for network communications with the networked database for accessing data from and storing data in the networked database, and
    (c) wherein the computer implemented method comprises the steps of,
        (i) providing a user interface including,
            (A) one or more user interface areas configured to allow for creation of a structured note representing documentation, and
            (B) one or more user interface areas configured to allow for selection, during the creation of the structured note, of one or more categories for which data is stored in the networked database, (ii) receiving, via the user interface provided in said step (i), a selection of one or more of the categories, (iii) accessing data that has been previously stored in the networked database, that is associated with a patient for which a structured note representing documentation is being created, and that corresponds to the one or more categories of the selection of said step (ii), (iv) presenting, during the creation of the structured note via the user interface, the data accessed from the networked database in said step (iii), (v) receiving, via the user interface provided in step (i), input for creating the structured note, the structured note including information associated with the one or more categories of the selection of said step (ii), (vi) in response to user input, storing in the networked database the structured note as a part of documentation stored in a record for the patient, and (vii) in conjunction with the storing of the structured note in said step (vi), automatically storing in the networked database, as a part of the record for the patient, information from the structured note in a second area of the record, the second area being determined based on predetermined system administrator settings and the one or more categories of the selection of said step (ii).

2. The apparatus of claim 1, wherein the one or more categories comprises at least one of the following predetermined categories: health issues, past medical history, outpatient medications, prescriptions, orders, care providers, significant events, allergies, patient problems, and flowsheet observations.

3. The apparatus of claim 1, wherein the user interface provides a first display area displaying categories corresponding to a plurality of fields in an electronic patient record, and wherein the selection of one of the fields pulls one or more rows of data from the electronic patient record into a user interface area for display.

4. The apparatus of claim 1, wherein the computing device is configured for network communications with the networked database over the Internet.

5. The apparatus of claim 1, wherein the computing device is configured for network communications with the networked database over a local area network.

6. The apparatus of claim 1, wherein the computing device is a handheld computing device.

7. The apparatus of claim 1, wherein the computing device is a workstation.

8. The apparatus of claim 1, wherein said step (vi) is performed upon selection of a user interface element representing user instruction to save the structured note to the networked database.

9. The apparatus of claim 1, wherein said step (vii) comprises pushing data from the structured note to one or more fields of an electronic patient records other than a documentation field storing clinical documentation.

10. A computer implemented method for storing information regarding a patient in a database in the form of an electronic patient record, comprising the computer implemented steps of:

(a) presenting, via an electronic display of a computing platform, a user interface including, (i) one or more user interface areas configured to allow for creation of a structured note representing clinical documentation associated with the patient, and (ii) one or more user interface areas configured to allow for selection of one or more categories for which data associated with patients is stored, (b) receiving, via the user interface of the computing platform presented in said step (a), a selection of one or more of the categories, (c) accessing data that has been previously stored, that is associated with the patient, and that corresponds one or more categories of the selection of said step (b), (d) presenting, via the computing platform, the data accessed in said step (c), (e) receiving, via the computer platform, input for creating the structured note, the structured note including information associated with the one or more categories of the selection of said step (b), (f) in response to user input, storing the structured note in the database as a part of an electronic patient record of the patient, and (g) in conjunction with the storing of the structured note in said step (f), automatically storing by one or more processors information from the structured note in a second area of the electronic patient record, the second area determined based on predetermined system administrator settings and the one or more categories of the selection of said step (b).

11. The computer implemented method of claim 10, wherein the user interface provides a first display area displaying categories corresponding to a plurality of fields in the electronic patient record, and wherein the selection of one of the fields pulls one or more rows of data from the electronic patient record into a user interface area for display on the computing platform.

12. The computer implemented method of claim 10, wherein the electronic patient record comprises rows and columns of data; wherein the method comprises selecting, from a menu of categories corresponding to a plurality of separate locations in the electronic patient record, a field for which to add documentation regarding the patient; wherein the selection of the field pulls one or more rows of data from the electronic patient record into a user interface for display of data therefrom on the computing platform; and wherein the documentation entered via the computing platform regarding a selected category is pushed to both the location of the electronic patient record directed to clinical documentation and to the location in the electronic patient record directed to the selected category.

13. The computer implemented method of claim 12, wherein said step (g) comprises pushing data from the structured note to one or more fields of the electronic patient records other than a documentation field where clinical documentation is stored.

14. An information system comprising:

(a) a database storing patient data, and (b) a plurality of user computing devices operatively connected to the database for reading data from and writing data to the database, each user computing device comprising a processing unit, a memory, and a display, (c) wherein the memory of each user computing device contains machine readable instructions executable by the processing unit for performing a computer implemented method comprising the steps of:

(i) providing, (A) one or more user interface areas configured to allow for creation of a structured note representing clinical documentation of a patient, and (B) one or more user interface areas configured to allow for selection, during the creation of the structured note, of one or more categories for which data associated with patients is stored in the database, (ii) receiving, via the user interface areas provided in said step (i), a selection of one or more of the categories, (iii) accessing data that has been previously stored in the database, that is associated with a patient for which a structured note representing clinical documentation is being created, and that corresponds to the one or more categories of the selection of said step (ii), (iv) presenting, during the creation of the structured note via the user interface areas provided in said step (i), the data accessed from the database in said step (iii), (v) receiving, via the user interface areas provided in step (i), input for creating the structured note, the structured note including information associated with the one or more categories of the selection of said step (ii), (vi) in response to user input, storing in the database the structured note as a part of clinical documentation of the patient stored in the database, and (vii) in conjunction with the storing in said step (vi) of the structured note in the database as a part of clinical documentation of the patient, further automatically storing in the database, as additional data pertaining to the patient, information from the structured note as part of one or more categories determined based on predetermined system administrator settings and the one or more categories of the selection of said step (ii).

15. The system of claim 14, wherein one or more of the user computing devices is configured for network communications with the networked database over the Internet.

16. The system of claim 14, wherein one or more of the user computing devices is configured for network communications with the networked database over a local area network.

17. The system of claim 14, wherein one or more of the user computing devices comprises a handheld computing device.

18. The system of claim 14, wherein one or more of the user computing devices comprises a workstation.

19. The system of claim 14, wherein said step (vi) is performed upon selection of a user interface element representing user instruction to save the structured note to the networked database.

20. The system of claim 14, wherein said step (vii) comprises pushing data from the structured note to one or more fields of an electronic patient record other than a documentation field where clinical documentation is stored.

* * * * *

UNITED STATES PATENT AND TRADEMARK OFFICE
CERTIFICATE OF CORRECTION

| | | |
|---|---|---|
| PATENT NO. | : 8,566,123 B2 | Page 1 of 1 |
| APPLICATION NO. | : 13/621119 | |
| DATED | : October 22, 2013 | |
| INVENTOR(S) | : Richard P. Mansour et al. | |

It is certified that error appears in the above-identified patent and that said Letters Patent is hereby corrected as shown below:

On the Title Page, Item (75), line 2, In the Inventors list, delete "Mullehhour" and insert --Mullenhour--.

Signed and Sealed this
Twenty-seventh Day of May, 2014

Michelle K. Lee
*Deputy Director of the United States Patent and Trademark Office*